United States Patent [19]
Dyke

[11] Patent Number: 6,146,640
[45] Date of Patent: Nov. 14, 2000

[54] IMMUNE SYSTEM CATALYST

[76] Inventor: John Paul Dyke, 5365 Linsey Lakes Dr., Glen Allen, Va. 23060

[21] Appl. No.: 09/386,363

[22] Filed: Aug. 31, 1999

Related U.S. Application Data

[60] Provisional application No. 60/098,587, Aug. 31, 1998.

[51] Int. Cl.[7] ............................ A61K 35/78; A61K 7/48; A01N 25/34
[52] U.S. Cl. ......................... 424/195.1; 424/401; 424/404
[58] Field of Search ................................ 514/859; 426/72, 426/248, 311; 424/404, 613, 195.1, 401

[56] References Cited

U.S. PATENT DOCUMENTS

| | | | |
|---|---|---|---|
| 4,826,681 | 5/1989 | Jacquet et al. | 424/613 |
| 5,744,150 | 4/1998 | Cercone | 424/404 |

FOREIGN PATENT DOCUMENTS

| | | | |
|---|---|---|---|
| 5320062 | 12/1992 | Japan | A23L 1/30 |
| 2139890 | 11/1984 | United Kingdom | A61K 31/23 |

OTHER PUBLICATIONS

Grieve, M. A Modern Herbal pp. 475, 601–602, 1996.

Moeller et al. AUS Lab. Der Henkel KGAA, Duesseldorf. 91 (8) pp. 295–305, 1989.

*Primary Examiner*—Jon P. Weber
*Assistant Examiner*—Patricia Patten
*Attorney, Agent, or Firm*—Hunton & Williams

[57] ABSTRACT

The present invention relates to a therapeutic composition for treating a wide variety of medical conditions, in particular a topical therapeutic composition for treatment of acne and other skin lesions/conditions. The invention also relates to methods of treatment utilizing this composition. The composition comprises, in a concentrate form, Tarrow Root Extract, Kafferlime Leaf Extract, iodine, and optionally Vitamin E. The composition can be further diluted with hydrogen peroxide to prepare a ready-to-use-solution.

23 Claims, No Drawings

IMMUNE SYSTEM CATALYST

RELATED APPLICATIONS

This application claims priority from a provisional application, Ser. No. 60/098,587, filed on Aug. 31, 1998, the entire contents of which are incorporated herein by reference in a manner consistent with this application.

FIELD OF THE INVENTION

The present invention relates to a therapeutic composition (and/or compositions) for treating a wide variety of medical conditions, in particular a topical therapeutic composition for treatment of acne and other skin lesions/conditions. The invention also relates to method of treatment utilizing such a composition. The composition comprises, in a concentrate form, Tarrow Root Extract, Kafferlime Leaf Extract, iodine, and optionally Vitamin E.

BACKGROUND OF THE INVENTION

Traditional medical approaches for the treatment of skin, tissue, and/or membrane conditions use chemicals specific to a particular invading agent of disease, toxicity, poison, or organic form. These approaches generally involve the use of antibiotics, steroids, inoculations, immunizations, chemotherapy, radiation or drugs designed for certain agents or symptoms. However, these methodologies often have undesirable and destructive side effects. In particular, these approaches have limited success and can leave irritations, scar tissue, or other irreversible conditions.

Therefore, there remains a need for a therapeutic composition for treating a wide variety of skin, tissues, and/or membrane conditions without the use of compounds or agents which have undesirable or destructive side effects.

It is therefor an object of the present invention to provide a therapeutic composition for the treatment of various medical conditions.

It is another object of the present invention to provide a therapeutic composition for the treatment of various medical conditions which is substantially non-irritating and reduces and/or reverses scar formation.

It is another object of the present invention to provide methods for the treatment of acne and other skin lesions and conditions.

It is another object of the present invention to provide methods of the treatment of acne and other skin lesions or conditions whereby the methods are substantially non-irritating to the user and reduce and/or reverse scar formation.

These and other objects of this invention will become apparent in light of the following disclosure.

SUMMARY OF THE INVENTION

The present invention relates to a therapeutic composition for treating a variety of medical conditions comprising, in concentrate form: (a) Tarrow Root Extract; (b) Kafferlime Leaf Extract; (c) iodine (or iodine solution); and optionally (d) Vitamin E. The concentrate composition can be further formulated with hydrogen peroxide to produce a final, ready-to-use composition (or solution).

The present invention also relates to methods of treatment of various medical conditions, including acne and skin lesions, utilizing the composition.

Further, the present invention relates to methods for making a therapeutic concentrate composition comprising the steps of:

a) bringing a mixture of Tarrow Roots, Kafferlime Leaves, and water to a boil;
b) simmering the mixture of step (a) to form an extract;
c) collecting the extract of step (b) by removing the Tarrow Roots and Kafferlime Leaves from the extract;
d) adding iodine (or an iodine solution) to the extract from step (c) to form a therapeutic concentrate composition.

The present invention also relates to a method for making a therapeutic ready-to-use composition (or preparation) comprising the steps of:

a) bringing a mixture of Tarrow Roots, Kafferlime Leaves, and water to a boil;
b) simmering the mixture of step (a) to form an extract,
c) collecting the extract of step (b) by removing the Tarrow Roots and Kafferlime Leaves from the extract;
d) adding iodine (or an iodine solution) to said extract from step (c) to form a concentrate composition;
e) diluting the concentrate composition of step (d) with hydrogen peroxide to form a therapeutic ready-to-use composition.

DETAILED DESCRIPTION OF THE INVENTION

It has surprisingly been found that a composition comprising a combination of Tarrow Root Extract, Kafferlime Leaf Extract, iodine (or an iodine solution), and optionally Vitamin E, is highly efficacious for the treatment of various medical conditions, including, but not limited to, acne and other skin lesions. The composition of the present invention can be prepared as a concentrate solution or as a diluted, ready-to-use preparation.

The terms "composition" or "therapeutic composition" and "compositions" or "therapeutic compositions", respectively, are used interchangeably herein. Thus, the plural includes the singular and the singular includes the plural form of the respective terms.

The therapeutic compositions of the present invention can be used alone or together with any other medical and treatment approach. No adverse side effects or problems associated with the use of the therapeutic compositions are known. Further, use of the therapeutic compositions to treat acne and other skin lesions/conditions can be effective to achieve at least about 50% condition correction within 3 or 3–5 days of treatment application.

While not being bound by theory, it is believed that compositions of the present invention act as antioxidants and also promote sustained oxygenation. It is also believed that the compositions aid the body in fighting off and/or killing harmful agents, in neutralizing and correcting side effects of harmful agents, and in repairing skin, tissues, and membranes at the cellular level. Further, it is believed that the compositions of the present invention have extensive anti-inflammatory properties. It has surprisingly been found that the compositions of the present invention work more rapidly than existing approaches substantially without any undesirable side effects.

The invention is primarily directed to a liquid composition useful for treating a variety of medical conditions. In particular, the composition is a therapeutic composition effective in treatment against bacteria, viruses, spores, fungi, molds, yeasts, protozoa, toxins (both organic and inorganic), warts, microbes, microbial, tumors, cancers, parasites, and poisons. It is also effective in healing and repair of skin, tissues, and/or membranes damaged by the aforementioned agents, as well as by burns (first, second or third degree); lesions; sores; lacerations; allergic skin, tissue, and/or membrane reactions; harmful reactions to medications, drugs and chemicals (both organic and inorganic); and by other harmful agents. Further, the composition of the invention is useful in healing and repairing damage caused by exposure to light, radiation, electromagnetic currents, wind, fire, water, pressure changes (complications of compression and decompression), fluid retention, blood clots, and any other agent or cause of illness, destruction, lack of beneficial function, or threat of survival to skin, membranes, tissues, and related parts, both internally (i.e., mucus membranes, nasal membranes, vaginal tissues and membranes, anal tissues and membranes, and interior ear structures) and externally.

Further, without wishing to be bound by any theory of operability, it is believed that the therapeutic compositions of the present invention also act as a catalyst to the human immune system and body to produce antibodies, chemical reactions, anti-toxins and body-functions to kill, neutralize and/or terminate and excrete or discharge invading and/or damaging microorganisms, toxins, chemical and agents of destruction. Additionally, it is believed that the therapeutic compositions of the present invention have anti-inflammatory properties.

The therapeutic compositions of the present invention are also microbicidal and bacteriostatic, and kill gram-positive and gram-negative bacteria, fungi, viruses, protozoa, and yeasts, and are anti-ineffective as well. The therapeutic compositions are efficacious in speeding up recovery, healing, and repair of damaged areas substantially without scar tissue forming or to much less extent that with previously known treatment methods and compositions. Repair, healing and correction can be measured and observed in hours and days. Dangerous and/or adverse side effects associated with the use of the therapeutic compositions are not known to exist.

As used herein the term "therapeutic composition" means a composition useful for treating skin, tissues, or membranes, both internally and externally.

The term "topical application", as used herein, means to apply or spread the compositions of the present invention to the surface of the skin, tissues, or membranes, both internally and externally.

As used herein the term "therapeutically effective amount" means an amount effective to treat the target medical condition.

The term "pharmaceutically-acceptable", as used herein, means that the compositions or components thereof so described are of sufficiently high purity and suitable for use in contact with skin, tissues, or membranes without undue toxicity, incompatibility, instability, allergic response, and the like.

Tarrow Root Extract

One component of the compositions of the present invention is Tarrow Root Extract. The compositions of the present invention comprise a therapeutically effective amount of Tarrow Root Extract for the treatment of the target medical condition which is dependent on a number of factors, including, but not limited to, the severity of the condition to be treated and the duration of treatment.

The Tarrow Root Extract can be prepared by any method known in the art. The Tarrow Root Extract is preferably prepared from Tarrow Root ripe for consumption, with the brown outer thin surface covering removed, e.g., by shaving off, which has been cut into small, 1/8 to 1/4 inch thick sections. Preferably, the shaved and cut Tarrow Root is mixed with an amount of water (preferably deionized, distilled, or filtered water) approximately equal to about 40% to about 80% of the desired volume of the final therapeutic concentrate composition. The mixture should be brought to a boil (at about 212° F.) in a loosely covered container, and then simmered for approximately 20 to approximately 40 minutes, preferably approximately 30 minutes, with the contents of the container being stirred about every 5–15 minutes, preferably about every 10 minutes, during the simmer period. At the end of the simmer period, the contents of the container are preferably allowed to cool and the Tarrow Root Extract collected by removing, e g, straining, the Tarrow Root, and any other large solids, from the extract broth. The extract broth will generally contain small residual solids and particles which can further be removed, e g., through filtering, if desired.

A wide range of Tarrow Root concentrations can be utilized in the preparation of the Tarrow Root Extract by the preferred method detailed above, depending upon a number of factors including, but not limited to, the boiling and simmering conditions (i.e., temperature, pressure, duration, etc.). The Tarrow Root sections used to prepare the Tarrow Root Extract are preferably used in an amount of from about 40 mg/cm$^3$ to about 1200 mg/cm$^3$, more preferably from about 500 mg/cm$^3$ to about 1200 mg/cm$^3$, and most preferably from about 500 mg/cm$^3$ to about 1000 mg/cm$^3$ of Tarrow Root, based on the volume of the Tarrow Root/water mixture to be simmered.

Kafferlime Leaf Extract

The compositions of the present invention also comprise Kafferlime Leaf Extract, an extract from eatable leaves picked from Kafferlime Trees. The compositions of the present invention comprise a therapeutically effective amount of Kafferlime Leaf Extract, also known as Bai Yanang Leaf Extract, for the treatment of the target medical condition which is dependent on a number of factors, including, but not limited to, the amount of Tarrow Root Extract used, the severity of the condition to be treated and the duration of treatment.

The Kafferlime Leaf Extract can be prepared by any method known in the art. Once picked from the Kafferlime Trees, the Kafferlime Leaves are preferably kept frozen at about 0° F. to about −10° F. until they are ready for use. Fresh, non-frozen Kafferlime Leaves may also be used. Further, prior to use, the Kafferlime Leaves are preferably rinsed with cool water. The Kafferlime Leaf Extract is preferably prepared by a method similar to that detailed above for preparing the Tarrow Root Extract, wherein the rinsed Kafferlime Leaves are mixed with an amount of water (preferably deionized, distilled, or filtered water) approximately equal to about 40% to about 80% of the desired volume of the final therapeutic concentrate composition. The mixture should be brought to a boil (at about 212° F.) in a loosely covered container, and then simmered for approximately 20 to approximately 40 minutes, preferably approximately 30 minutes, with the contents of the container being stirred about every 5–15 minutes, preferably about every 10 minutes, during the simmer period. At the end of the simmer period, the contents of the container are preferably allowed to cool and the Kafferlime Leaf Extract collected by removing, e.g., straining the Kafferlime Leaves, and any other large solids, from the extract broth. Again, the extract broth will generally contain small residual solids and particles which can further be removed, e.g., through filtering, if desired.

A wide range of Kafferlime Leaf concentrations can be utilized in the preparation of the Kafferlime Leaf Extract by the preferred method detailed above, depending upon a number of factors including, but not limited to, the boiling and simmering conditions (i.e., temperature, pressure, duration, etc.). The Kafferlime Leaves used to prepare the Kafferlime Leaf Extract are preferably used in an amount of from about 30 mg/cm$^3$ to about 100 mg/cm$^3$, more preferably from about 40 mg/cm$^3$ to about 100 mg/cm$^3$, and most preferably about 40 mg/cm$^3$ to about 80 mg/cm$^3$ of Kafferlime Leaves, based on the volume of the Kafferlime Leaf/water mixture to be simmered.

Alternatively, the Tarrow Root Extract and the Kafferlime Leaf Extract can be prepared together by utilizing a single mixture as described below and exemplified in Example 1. For example, in one embodiment the shaved and cut Tarrow Root and rinsed Kafferlime Leaves are mixed with an amount of water (preferably deionized, distilled, or filtered water) approximately equal to about 40% to about 80% of the desired volume of the final therapeutic concentrate composition. The mixture is brought to a boil (at about 212° F.) in a loosely covered container, and then simmered for approximately 20 to approximately 40 minutes, preferably approximately 30 minutes, with the contents of the container being stirred about every 5 to about every 15 minutes, preferably approximately every 10 minutes, during the simmer period. At the end of the simmer period, the contents of the container are preferably allowed to cool and the Tarrow Root/Kafferlime Leaf Extract collected by removing (e.g., through straining) the Tarrow Root, Kafferlime Leaves, and any other large solids, from the extract broth. Again, the extract broth will generally contain small residual solids and particles which can further be removed, e g, through filtering, if desired.

However, in any embodiments of the invention such small residual solids and particles (also collectively referred to here as "granular particulate matter") are preferably not removed if the ready-to-use composition of the invention is intended for topical use, or to treat acne and other skin lesions or conditions.

The combined Tarrow Root/Kafferlime Leaf Extract can be prepared from a mixture comprising from about 400 mg/cm$^3$ to about 600 mg/cm$^3$, more preferably from about 460 mg/cm$^3$ to about 530 mg/cm$^3$, and most preferably about 500 mg/cm$^3$ of Tarrow Root based on the total volume of the Tarrow Root/Kafferlime Leaf/water mixture to be simmered; from about 32 mg/cm$^3$ to about 48 mg/cm$^3$, more preferably from about 37 mg/cm$^3$ to about 43 mg/cm$^3$, and most preferably about 40 mg/cm$^3$ of Kafferlime Leaves based on the total volume of the Tarrow Root/Kafferlime Leaf/water mixture to be simmered; and an amount of water equal to about 80% of the desired volume of the final therapeutic concentrate solution.

Other Components

The therapeutic compositions of the present invention also comprise a therapeutically effective amount of iodine (or iodine solution) for the treatment of the target medical condition. The iodine is preferably an iodine solution, and can be any iodine solution known in the art. For example, the iodine solution can be Tincture of Iodine Solution (2% iodine, 2.4% sodium iodide), Strong Tincture of Iodine Solution (7% iodine, 5% potassium iodide), povidone-iodine solution (a water soluble complex which can contain 5%, 7.5% or 10% povidone-iodine and inactive ingredients such as citric acid, dibasic sodium phosphate and glycerin). Most preferably, the iodine solution is 10% povidone-iodine solution (i.e., Betadine® with 9–12% available iodine).

Optionally, the therapeutic compositions of the present invention can include a therapeutically effective amount of Vitamin E for treatment of the target medical condition.

Without wishing to be bound by theory, it is believed that the Vitamin E smooths the skin, tissue, or membrane to be treated and to enhance scar prevention/repair. The Vitamin E can be any Vitamin E known in the art and is preferably dl-Alpha Tocopheryl Acetate with glycerin, purified water and soybean oil to place it in aqueous form.

Further, when the therapeutic compositions of the present invention are formulated as a ready-to-use preparation, the composition also can include hydrogen peroxide. The hydrogen peroxide is preferably a 3% solution, and can contain 0.001% phosphoric acid as a stabilizer and purified water.

Topical Preparations

The compositions of the present invention can also preferably comprise a topical carrier. The term "topical carrier", as used herein, is well-known to one of ordinary skill in the art, and means one or more compatible solid or liquid filler diluents or vehicles which are suitable for administration to skin, tissues, or membranes. The term "compatible", as used herein, means that the components of the topical carrier are capable of being commingled with the components of the present invention, and with each other, in a manner such that there is no interaction which would substantially reduce the therapeutic efficacy of the composition under ordinary use situations. The topical carrier must be pharmaceutically acceptable carrier. The term "pharmaceutically-acceptable", as used herein, means that the topical carrier must be of sufficiently high purity and suitable for use in contact with skin tissues, or membranes without undue toxicity, incompatibility, instability, allergic response, and the like.

In a preferred embodiment, the therapeutic compositions of the subject invention are administered topically to a biological subject, i.e., by the direct laying on or spreading of the composition on the target skin, tissues, or membranes of the subject. Most preferably, the topical compositions useful in the subject invention involve compositions suitable for topical application to human skin, tissues, or membranes. The topical compositions useful in the subject invention formulated as solutions typically include a pharmaceutically-acceptable aqueous or organic solvent. Water is a preferred solvent.

The preferred topical compositions useful in the subject invention can be made into a wide variety of product types. These include, but are not limited to, lotions, creams, gels, sticks, sprays, ointments, pastes, mousses, and cosmetics. These product types can comprise several types of carrier systems including, but not limited to solutions, emulsions, gels, solids, and liposimes. Also useful are cleansing compositions which also deliver the components of the present invention to the skin during the cleansing process. The physical form of the cleansing compositions is not critical. The cleansing compositions can be, for example, formulated as toilet bars, liquids, shampoos, conditioners, pastes, or mousses. Rinse-off cleansing compositions, such as shampoos, require a delivery system adequate to deposit sufficient levels of active ingredients on the skin and scalp. The cleansing compositions useful in the subject invention can optionally contain, at their art-established levels, materials which are conventionally used in cleansing compositions.

Method of Preparing the Concentrate Solution and the Ready-to-us Preparation

The therapeutic concentrate composition (or solution) can be prepared by bringing a mixture of Tarrow Roots, Kafferlime Leaves, and water to a boil; simmering the mixture to form an extract; collecting the extract by removing, e.g., straining, the Tarrow Roots and Kafferlime Leaves from the extract; and adding iodine to the extract to form a therapeutic concentrate composition. In a particularly preferred embodiment, Vitamin E is also added to the Tarrow Root Extract/Kafferlime Leaf Extract mixture along with the iodine.

When prepared from the combined Tarrow Root/Kafferlime Leaf Extract, the therapeutic concentrate composition of the present invention can comprise from about 50 to about 68 parts, preferably about 60 parts, of combined Tarrow Root/Kafferlime Leaf Extract; from about 32 to about 50 parts, preferably about 40 parts, of iodine solution; and optionally up to about 10 parts, preferably up to about 5 parts, more preferably up to about 1 part, most preferably about 0.83 parts, of Vitamin E, based on the total volume of concentrate.

Alternatively, the therapeutic concentrate composition of the present invention can be prepared by mixing separately prepared Tarrow Root Extract and Kafferlime Leaf Extract with iodine, and optionally, Vitamin E. The separate Tarrow Root Extract and Kafferlime Leaf Extract can be prepared as described above. The therapeutic concentrate composition prepared from the separate Tarrow Root Extract and Kafferlime Leaf Extract comprises from about 25 to about 34 parts, preferably about 30 parts, of Tarrow Root Extract; from about 25 to about 34 parts, preferably 30 parts, Kafferlime Leaf Extract; from about 32 to about 50 parts, preferably about 40 parts, of iodine solution; and optionally, up to about 10 parts, preferably up to about 5 parts, more preferably up to about 1 part, most preferably about 0.83 parts, Vitamin E, based on the total volume of concentrate.

The ready-to-use preparation of the therapeutic compositions of the present invention can be prepared by diluting the therapeutic concentrate composition with hydrogen peroxide, preferably at a dilution ratio (concentrate: hydrogen peroxide) of from about 1:0.5 to about 1:5, more preferably at a ratio of from about 1:1 to about 1:4, and most preferably at a ratio of about 1:2 by volume. The ready-to use preparation of the composition preferably comprises from about 5 to about 25, preferably from about 5 to about 20, and most preferably about 9.4 parts by volume of Tarrow Root Extract; from about 5 to about 25, preferably from about 5 to about 20, and most preferably about 9.4 parts by volume of Kafferlime Leaf Extract; from about 6 to about 32, preferably about 8 to about 25, and most preferably about 12.5 parts by volume of iodine solution; and from about 18 to about 84, preferably about 35 to about 82, and most preferably about 68.7 parts by volume hydrogen peroxide solution. Optionally, the ready-to-use preparation of the composition can further include Vitamin E. The Vitamin E is preferably present in the ready-to-use preparation in an amount of up to about 6 parts, preferably up to about 1 part, more preferably about 0.67 parts and most preferably about 0.41 parts by volume.

Methods of Treatment of Acne and Other Skin Lesions and Conditions

The compositions of the present invention are useful for preferably treating acne and other skin lesions and conditions. To obtain a therapeutic benefit, a therapeutically effective amount of the composition of the present invention is applied to the skin or affected area.

In a particularly preferred embodiment, the ready-to-use preparation of the therapeutic composition of the present invention is applied once a day for three consecutive days for at least 20 minutes and up to one hour. (Please note that if a therapeutic composition were made into a gel, cream, lotion, salve, ointment or other form, the time of application to the area for treatment can go beyond one hour). then, after those initial three days in a row, apply 1 day apart, 2 days apart, 3 days apart, 4 days apart, 5 days apart, 6 days apart for 4 applications, 14 days apart for 4 applications, then 29 days apart until the last application is almost 6 months from the beginning (days in numbers are 1, 2, 3, 5, 8, 12, 17, 23, 30, 37, 44, 51, 66, 81, 06, 111, 141, 171, thus about 6 months).

To apply the therapeutic composition, the skin, membrane or affected tissue area is immersed, for instance, by saturating a wrapping (e.g., 4 to 6 layers of cotton gauze or 6 sheets of paper towels, unscented and without colors from stains) with the ready-to-use preparation covering the skin, membrane, or tissue area to be treated. If necessary, during treatment additional ready-to-use preparation can be added to the wrap. It is important to immerse the skin, membrane or tissue area with the ready-to-use preparation of the invention.

Further, a plastic wrap can be placed over the wrapping to help reduce evaporation and to make the best use of the localized rise in treatment area temperature, that can occur. This rise usually will not go beyond 105° F. The range is usually 100° F. to 102° F. While not being bound by theory, it is believed that this temperature rise aids in treatment of the acne or skin lesions promoting the dilation of the pores and/or perspiration. The rise in temperature is not permanent and lasts for a limited time, depending on the condition, most usually up to 20 minutes, even though the treatment may last one hour. There can be a slight tingle sensation toward the surface, during treatment.

After the treatment time has expired, the wrapping can be removed and the residue rinsed off with water and optionally with a mild soap. If treating areas near the eyes, the use of protective eye wear is suggested.

The therapeutic compositions of the present invention relieve, heal and/or correct pruritus (itching usually disappears seconds after application and does not return even after treatment is ended and the area has been washed with water and shampoo, or soap), inflammation, swelling, edema, papulae, bullae and other forms of skin elevations, eruptions, and/or growths, irregularities in skin pigmentation, secretions from elevations, rashes and other irregularities of the skin, membranes and/or tissues.

The therapeutic compositions of the present invention can also be used to treat vaginal disorders, such as yeast infections, by mixing 240 cc (8 oz) of a ready-to-use preparation of the composition (the hydrogen peroxide 3% solution was added to the rest of the formula and the granular particulate matter in the invention liquid has been strained out) with 480 cc (16 oz) of distilled water. The treatment composition should then be applied twice a day, each time for up to ten minutes, for two days, once in the morning and once at night before going to sleep by douching into the vaginal opening, thus, into the vagina. Preferably, this should be done in a prone position with the subject on her back and knees bent. After the treatment period, the therapeutic composition can be allowed to drain out and rinsed off.

Further, the therapeutic compositions can be used to treat ear disorders, such as otitis media, middle ear infection. Again, mix 240 cc (8 oz) of a ready-to-use preparation of the therapeutic composition (the hydrogen peroxide 3% solution was added to the rest of the formula and the granular particulate matter in the concentrate composition has been strained out), with 480 cc (16 oz) of distilled water. Allow this mix to come to room temperature and irrigate the infected ear or ears. Use 180 cc (6 oz) at a time, two times a day for 2 days. Space applications 12 hours apart. Use 180 cc (6 oz) per ear.

Other Uses

The compositions of the present invention are also useful in treating other disorders, conditions, and/or diseases such as: lesions (macules, papules, nodules, vesicles, pustules, scaling, crusting, ulcers, scars, hemorrhoids), acne, atopic dermatitis, erythema multiforme, erythema nodusum, lichen planus, chronic discoid LE, photosensitivity reactions, pityriasis rosea, psoriasis, rosacea, miliaria, intertrigo, erythema intertigo, chafing, pruitus, sebaceous (keratmous) cyst, hyperhidrosis, vitiligo, warts [(*verrucae vulgares,* filiform, moist or "veneral" warts (*condylomata acuminata*), plantar warts, mosaic, flat, unusual types)], acne (grade 1, grade II, grade III, *S. albus,* Corynebacterium, *C. acnes*), rosacea, bacterial skin infections, impetigo, *impetigo contagiosa,* ecthyma, ulcerative impetigo, erythrasma, cellutitis, erysipelas, furuncles, carbuncles, *hidradenitis suppurativa,* paronychial infections, follicular infections, *pyogenic granuloma,* superficial fungus infections (dermtophytids or "id" eruptions, *tinea corporis* or ringworm of the body, *tinea pedis* or ringworm of the foot, *tinea unguium* or ringworm of the nails or onychomycosis, *tinea capitis* or ringwork of the scalp, tinea tonsurans infections, *tinea favosa, tinea cruris* or *eczema marginatum* or jock strap itch or dhobie itch, *rinea barbae,* candidiasis or candidosis or moniliasis), scabies, pediculosis, *pediculosis capitis, pediculosis corporis, pediculosis pubis,* creeping eruption or cutaneous larva migrans, dermatitis, contact dermatitis or *dermatitis venenata,* atopic dermatitis or disseminated neuodermatitis, *sevorrheic dermatitis,* localized scratch dermatitis or localized neuodermatitis or lichen simplex chronicus, *nummular dermatitis, stasis dermatitis,* chronic dermatitis of hands and feet (including fungus infections, contact dermatitis due to primary irritants and sensitizing agents, nummular or atopic dermatitis, psoriasis and dermatitis repens), infantile dermatitis (including atopic, seborrheic infantile eczema, contact), drug eruption or *dermatitis medicamentosa* (including maculopapular rash, urticaria and angioedema, vesiculobullous eruptions, pustular eruptions and granulomas, erthema nodosum, lichen planus-like reactions, acneform eruptions, photosensitization), *erthema nososum, erthema multiforme* or *herpes iris* or erythema multiforme bullosum, *pityriasis rosea* or *pityriasis rubra, lichen planus* or lichen ruber planus, psoriasis, pemphigus, ichthyosis (or fish skin disease, xeroderma), callosity and/or corns, decubitis or bedsore or pressure sore or tropic ulcer, nevi, angiomas or hermangioma or *vevus vasculosus,* epithelioma including basal cell and squamous cell types, vaginal inflammation, nipple pain-fissures, mastitis, dyspareunia-vaginismus, vulvitis, vaginal carcinoma, canver of the vulva, trophoblastic disease or hydatidiform mole, endometrial carconima, cervical carcinoma, postmenopausal bleeding, vaginitis, neoplasms (adenocarcinoma of the endometrium, sarconas and mixed desodermal tumors), trichomonas vaginitis, vaginal mycosis, postmenopausal vaginitis, endocervicts, vaginal yeast infections, vaginal bacteria infections, acute external otitis (ear), forunculosis, otomycosis, aural eczematous dermatitis, aural herpes zoster, aural impetigo, tumors, myringitis, eustachitis or acute eustachian salpingitis, otisis media, acute serous otitis media, acute purulent (suppurative) otitis media, chronic secretory otitis media, chronic congestive otitis media, chronic purulent otitis media, mastoditis, acute and chronic mastoiditis, tinnitus, rhinoscleroma (nose), septal ulcer, allergic rhinitis (atopic or vasomotor rhinitis), arrophic rhinitis, polyps, chronic rhinitis or hypertropic rhinitis, epistaxis, bowen's disease, measles (rubeola, morbilli), german measles (rubella), roseola infantum (*exanthem subitum,* pseudorubella), chicken pox (varicella), herpes simplex (fever flister, cold sore), herpes zoster (shingles, zona, acute posterior gangliontis), smallpox (variola), scarlet fever (scariatina), drug rash, infectious monoucleosis, conjunctivitis, mumps (epidemic parotitis), yellow fever (fievre jaune, gelbesfieber, virus amaril), dengue (breakbone or dandy fever), rickettsial diseases [epidemic typhus, murine (endemic) typhus, Rocky Mountain spotted fever, South American spotted fever, fievre boutonneuse, Q fever, scrub typhus, trench fever, rickettsialpox], (caused also by toxin producing bacteria and by myobacteria), urticaria and angioedema (hives, giant urticaria, angioeurotic edema), atopic diseases, fungus diseases [including blastomycosis (North American blastomycosis, Gilchrist's disease)], paracoccidioidomycosis (South American blastomycosis, paracoccidioidal granuloma, Lutz-Splendore-Almeida disease), cryptococcosis (European blastomycosis, torulosis, Busse-Buschke's disease), sporotrichosis, candidasis (candidosis, moniliasis), geotrichosis, rhino sporidiosis, chromomycosis (chromoblastomycosis, varrucous dermatitis), oriental sore (cutaneous leishmaniasis, tropical sore, delhi or aleppo boil) a protozal disease, American leishmaniasis (espundia, forest yaws, uta, chiclera ulcer), worms entering body through the skin (including threadworm, hookworm, blood flukes), filariasis, dracunculiasis (dracontiasis, "tiery serpent"), sarcoidosis (Boeck's sarcoid, Besnier-Boeck-Schaumann disease), tumors, cysts, flat lesions in plane of skin (macule, infarct, sclerosis, telangiectasia), elevated lesions above plane of skin (vesicle and bulla, pustule, abscess, cyst, papule, wheal, plaque, nodule, vegetation, keratosis, desquanation (scales), exudate (crusts), lichenification), depressed lesions below plane of skin (atrophy, sclerosis, erosion, excoriation, scar, ulcer, sinus, gangrene).

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

Formulation

A preferred embodiment of the present invention can be prepared according to the following steps. As recited, 24, 240 cc (8 oz) batches can be preferably prepared.

(a) Take Tarrow Roots that are ripe for consumption, shave off the rough brown outer thin surface covering and discard the shavings.

(b) Cut, slice, and dice in ¼ inch thick sections and collect 750 g of these sections.

(c) Place these sections into a 2,000 cc (about 67 oz) container.

(d) Add 1,500 cc (50 oz) of distilled water to this container.

(e) Take 60 g of Kafferlime Leaves from Kafferlime Trees and rinse gently with cool running water in a colander and place the Leaves into the container which already has the Tarrow Root sections and distilled water.

(f) Place a loose covering lid onto the container to allow for venting. Bring the contents of the container to a boil at about 100° C. (212° F.) and then simmer gently for 30 minutes.

(g) At 10 minutes at 20 minutes, stir the contents of the container with a clean rod.

(h) At the end of 30 minutes, stop the simmer and allow the covered container to cool to room temperature.

(i) Strain the large solids from the extract broth and collect about 1,080 cc (36 oz) of the extract broth. The extract broth can contain residual particulate solids. Top off with distilled water to 1,080 cc if necessary and stir with a clean rod.
(j) Add 720 cc (24 oz) of povidone-iodine solution 10%, and stir with a clean rod.
(k) Add 9,600 IU (approximately 15 cc or 0.5 oz) of Vitamin E and stir with a clean rod.
(l) Aliquot 75 cc (2.5 oz) batches into 24 240 cc (8 oz) plastic or glass bottles.
(m) Add 165 cc (5.5 oz) of hydrogen peroxide solution to each 240 cc bottle.
(n) Cap bottle and shake. The composition is ready for use.

Example 2

Clinical Trials

The ready-to-use preparation of the therapeutic composition of the present invention prepared by the method of Example 1 was tested on 2 patients.

One patient had cystic and comedonal acne and had been on Accutane® 2 times in the past. She expressed desire to go on Accutane® a third time. She was asked and agreed to try this new product applied for 20 minutes a day for 3 days in a row. She reported that she was dramatically better and didn't need to go on Accutane® again.

The second patient had multiple flat warts (*verruca plana*) on the face. She had seen many doctors and had tried numerous therapies, including unusual herbal therapies as well as prescription drugs. She was treated with the therapeutic composition for several days in a row and then reported that she was at least 50% better (for the first time in at least a year).

The invention may be embodied in other specific forms without departing from the spirit or essential characteristics thereof. The present embodiments are, therefore, to be considered in all respects as illustrative and not restrictive, the scope of the invention being indicated by the appended claims.

What is claimed is:

1. A concentrate composition comprising:
   (a) Tarrow Root aqueous Extract;
   (b) Bai Yanang Leaf aqueous Extract; and
   (c) iodine solution.

2. The concentrate composition of claim 1 comprising from about 25 to about 34 parts by volume of Tarrow Root aqueous Extract; from about 25 to about 34 parts by volume of Bai Yanang Leaf aqueous Extract; and from about 32 to about 50 parts by volume of iodine solution.

3. The concentrate composition of claim 1 further including Vitamin E.

4. The concentrate composition of claim 3 wherein up to about 1 part by volume of Vitamin E is present.

5. The concentrate composition of claim 1 wherein the iodine solution is a 10% povidone-iodine solution.

6. A method for making the concentrate composition of claim 1 comprising the steps of:
   a) bringing a mixture of Tarrow Roots Bai Yanang Leaves, and water to a boil;
   b) simmering the mixture of step (a) to form an extract;
   c) collecting the extract of step (b) by removing the Tarrow Roots and Bai Yanang Leaves from the extract; and
   d) adding iodine solution to the extract from step (c) to form a concentrate composition.

7. The method of claim 6 wherein from about 400 mg/cm$^3$ to about 600 mg/cm$^3$ of Tarrow Root, and from about 32 mg/cm$^3$ to about 48 mg/cm$^3$ of Bai Yanang Leaves are present in the mixture of step (a), based on the total volume of the mixture of step (a).

8. The method of claim 6 further comprising the step of:
   e) adding Vitamin E to the concentrate composition of step (d).

9. A ready-to-use composition comprising:
   (a) Tarrow Root aqueous Extract;
   (b) Bai Yanang Leaf aqueous Extract;
   (c) iodine solution; and
   (d) hydrogen peroxide solution.

10. The ready-to-use composition of claim 9 comprising from about 5 to about 25 parts by volume of Tarrow Root aqueous Extract; from about 5 to about 25 parts by volume of Bai Yanang Leaf aqueous Extract; from about 6 to about 32 parts by volume of iodine solution, and from about 18 to about 84 parts by volume hydrogen peroxide solution.

11. The ready-to-use composition of claim 9 further including Vitamin E.

12. The ready-to-use composition of claim 11 further including up to about 1 part by volume of Vitamin e.

13. The ready-to-use composition of claim 9 wherein the iodine solution is a 10% povidone-iodine solutions.

14. The ready-to-use composition of claim 9 comprising about 5 to about 20 parts by volume of Tarrow Root aqueous Extract, about 5 to about 20 parts by volume of Bai Yanang Leaf aqueous Extract, about 8 to about 25 parts by volume of iodine solution, about 35 to about 82 parts by volume of hydrogen peroxide solution and up to about 6 parts by volume of Vitamin E.

15. The ready-to-use composition of claim 9 comprising about 9.4 parts by volume of Tarrow Root aqueous Extract, about 9.4 parts by volume of Bai Yanang Leaf aqueous extract, about 12.5 parts by volume of iodine solution, about 68.7 parts by volume of hydrogen peroxide solution and about 0.67 parts by volume of Vitamin E.

16. The ready-to-use composition of claim 9 which comprises about 0.41 parts by volume of hydrogen peroxide solution.

17. A method for treating acne on the skin of a subject comprising the step of applying the ready-to-use topical composition of claim 11 to the affected area of the skin.

18. A method for making the ready-to-use composition of claim 9 comprising the steps of:
   a) bringing a mixture of Tarrow Roots, Bai Yanang Leaves, and water to a boil,
   b) simmering the mixture of step (a) to form an extract;
   c) collecting the extract of step (b) by removing the Tarrow Roots and Bai Yanang Leaves from the extract,
   d) adding iodine solution to the extract from step (c) to form a concentrate composition,
   d) diluting the concentrate composition of step (d) with hydrogen peroxide solution to form a ready-to-use composition.

19. The method of claim 18 herein the concentrate composition is diluted with hydrogen peroxide in step (e) at the concentrate composition:hydrogen peroxide dilution ratio of from about 1:0.5 to about 1.5 by volume.

20. The method of claim 18 wherein the concentrate composition is diluted with hydrogen peroxide in step (e) at the concentrate composition:hydrogen peroxide dilution ratio of from about 1:1 to about 1:4 by volume.

21. The method of claim 18 wherein the concentrate composition is diluted with hydrogen peroxide in step (e) at the concentrate composition:hydrogen peroxide dilution ratio of about 1:2 by volume.

22. The method of claim 18 wherein from about 400 mg/cm$^3$ to about 600 mg/cm of Tarrow Root and from about 32 mg/cm$^3$ to about 48 mg/cm$^3$ of Bai Yanang Leaves are present in the mixture of step (a), based on the total volume of the mixture of step (a).

23. The method of claim 18, further comprising the step of adding Vitamin E to the concentrate composition of step (d).

* * * * *